United States Patent
Tsujita

(10) Patent No.: US 10,016,181 B2
(45) Date of Patent: Jul. 10, 2018

(54) ULTRASOUND DIAGNOSTIC APPARATUS AND ULTRASOUND THREE-DIMENSIONAL IMAGE CREATION METHOD

(71) Applicant: HITACHI, LTD., Chiyoda-ku, Tokyo (JP)

(72) Inventor: Takehiro Tsujita, Mitaka (JP)

(73) Assignee: HITACHI, LTD., Tokyo (JP)

( * ) Notice: Subject to any disclaimer, the term of this patent is extended or adjusted under 35 U.S.C. 154(b) by 517 days.

(21) Appl. No.: 14/431,362

(22) PCT Filed: Sep. 12, 2013

(86) PCT No.: PCT/JP2013/074740
§ 371 (c)(1),
(2) Date: Mar. 26, 2015

(87) PCT Pub. No.: WO2014/050601
PCT Pub. Date: Apr. 3, 2014

(65) Prior Publication Data
US 2016/0038124 A1 Feb. 11, 2016

(30) Foreign Application Priority Data
Sep. 26, 2012 (JP) .................................. 2012-213185

(51) Int. Cl.
*A61B 8/00* (2006.01)
*A61B 8/08* (2006.01)
(Continued)

(52) U.S. Cl.
CPC ............ *A61B 8/5215* (2013.01); *A61B 8/466* (2013.01); *A61B 8/483* (2013.01); *G06T 15/506* (2013.01);
(Continued)

(58) Field of Classification Search
CPC ..... A61B 8/5215; A61B 8/483; A61B 8/0866; A61B 8/466; G06T 15/506; G06T 19/00; G06T 2210/41
See application file for complete search history.

(56) References Cited

U.S. PATENT DOCUMENTS

| 5,497,776 A | 3/1996 | Yamazaki et al. |
| 2010/0185091 A1 | 7/2010 | Sumi et al. |

(Continued)

FOREIGN PATENT DOCUMENTS

| JP | 2000-254123 A | 9/2000 |
| JP | 2003-061956 A | 3/2003 |

(Continued)

OTHER PUBLICATIONS

Nov. 12, 2013 Search Report issued in International Patent Application No. PCT/JP2013/074740.

*Primary Examiner* — Joel Lamprecht
(74) *Attorney, Agent, or Firm* — Oliff PLC

(57) ABSTRACT

Provided is an ultrasound diagnostic apparatus capable of creating a three-dimensional image that expresses the shading effect due to leakage, absorption or others of light. The apparatus displays a three-dimensional image of an object based on luminance volume data, and includes: a light source information setting unit configured to set light source data indicating a property of a light source that is set in a three-dimensional space; an optical property setting unit configured to set a weight coefficient indicating an optical property of the luminance volume data with respect to the light source; an illuminance calculation unit configured to calculate an illuminance at a position corresponding to a coordinate of the luminance volume data, based on the optical data and the weight coefficient, and to create illuminance volume data based on the calculated illuminance; and (Continued)

a volume rendering unit configured to create the three-dimensional image from the data.

13 Claims, 14 Drawing Sheets

(51) Int. Cl.
*G06T 15/50* (2011.01)
*G06T 19/00* (2011.01)
(52) U.S. Cl.
CPC ............ *G06T 19/00* (2013.01); *A61B 8/0866* (2013.01); *G06T 2210/41* (2013.01)

(56) References Cited

U.S. PATENT DOCUMENTS

2011/0077526 A1* 3/2011 Zwirn ................. A61B 5/0095
600/459
2012/0253180 A1* 10/2012 Emelianov ........... A61B 8/0841
600/424

FOREIGN PATENT DOCUMENTS

| JP | 2006-130071 A | 5/2006 |
| JP | 2008-259697 A | 10/2008 |
| JP | 2010-188118 A | 9/2010 |

* cited by examiner

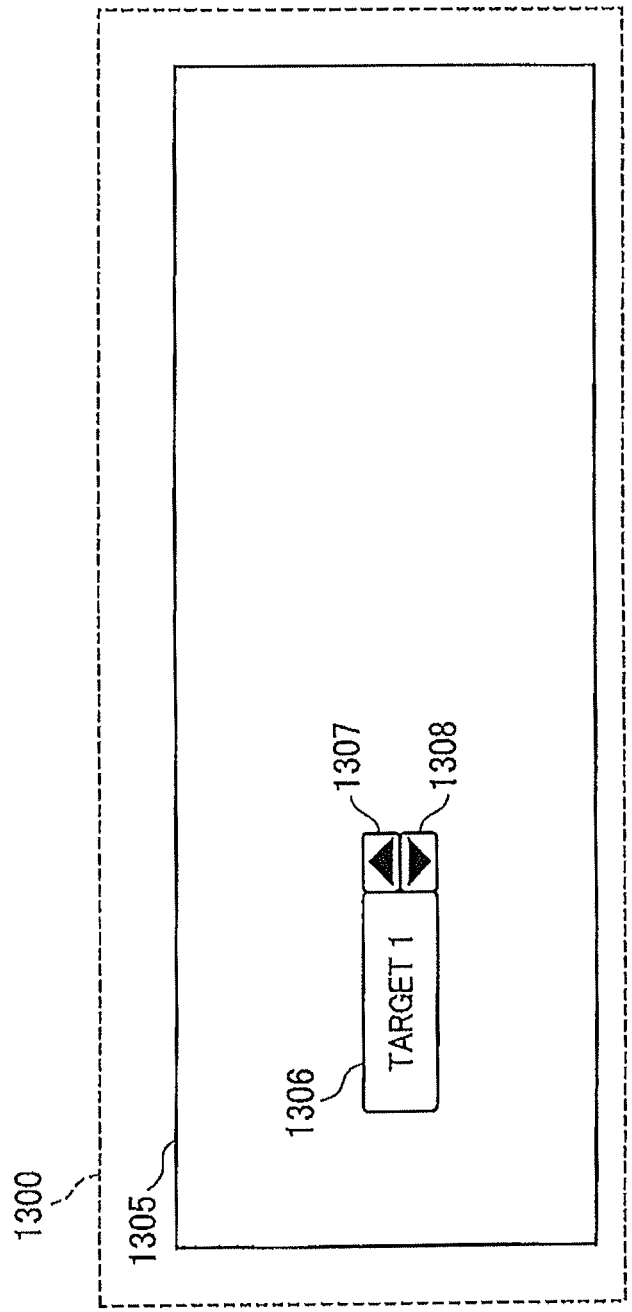

ULTRASOUND DIAGNOSTIC APPARATUS AND ULTRASOUND THREE-DIMENSIONAL IMAGE CREATION METHOD

TECHNICAL FIELD

The present invention relates to an ultrasound diagnostic apparatus, and particularly, to an ultrasound diagnostic apparatus that generates a three-dimensional projection image from intensity volume data of an ultrasonic wave.

BACKGROUND ART

An ultrasound diagnostic apparatus sends an ultrasonic wave to the inside of a diagnosing object by an ultrasound probe, receives a reflected echo signal which corresponds to a structure of a biological tissue from the inside of the diagnosing object, and forms a multi-planar reconstruction (B-mode) image, e.g., an ultrasonic multi-planar reconstruction (B-mode) image (B-mode image), or the like, to be displayed for a diagnosis.

In order to collect three-dimensional ultrasonic data, in the typical technique, three-dimensional data obtained by scanning a probe automatically or manually in a short axis direction is subject to coordinate conversion, thereafter ultrasonic image data is reconfigured in a visual line direction, and a three-dimensional image is created, thereby a surface of an object is observed.

Also, the recent typical technique is a technique called real-time 3D or 4D, in which signal processing described above is performed in real time, and a moving three-dimensional image is displayed.

These three-dimensional images are excellent at the delineation ability of a surface shape, and are useful in diagnosis of a disease about a fissure on the skin (a labial fissure, a palatal fissure or the like), which is conventionally difficult to diagnose from an ultrasound multi-planar reconstruction (B-mode) image displaying a single cross section region.

However, an ultrasound image has many artifacts unique to ultrasonic waves, such as speckle noises. Therefore, the image quality is improved by a smoothing process, but the smoothing process, as an opposite effect, makes a border continuous so that the fissure on the skin is continuously displayed.

As a method for solving this problem, of image processing apparatuses capable of a three-dimensional image display, there is an image processing apparatus that conducts both of the structure grasp and surface shape extraction for an inspection object and that can obtain a composition three-dimensional image with a good image quality (see Patent Literature 1, for example).

CITATION LIST

Patent Literature

Patent Literature 1: JP-A-2006-130071

SUMMARY OF INVENTION

Technical Problem

However, in the conventional ultrasound diagnostic apparatus (image processing apparatus), although it is possible to obtain a good image quality by conducting both of the structure grasp and surface shape extraction for an inspection object, it is impossible to set a light source in a volume rendering method and to obtain an image in which reality is improved by a shade and the like, unlike an optical photograph.

The present invention has been made for solving the conventional problems, and an object thereof is to provide an ultrasound diagnostic apparatus to create a three-dimensional image that expresses the behavior of light (leakage, absorption, scattering, reflection, or the like) in a tissue, and thereby reproduces a shade at a back portion of a tissue and a local shade appearing at a fissure on the skin, to express the shading effect due to the leakage, absorption or others of light.

Solution to Problem

An ultrasound diagnostic apparatus according to the present invention is an ultrasound diagnostic apparatus to display a three-dimensional image of an object based on intensity volume data, and includes: a light source information setting unit configured to set light source data indicating a property of a light source that is set in a three-dimensional space; an optical property setting unit configured to set a weight coefficient indicating an optical property of the intensity volume data with respect to the light source; an illuminance calculation unit configured to calculate an illuminance at a position corresponding to a coordinate of the intensity volume data, based on the optical data and the weight coefficient, and to create illuminance volume data based on the calculated illuminance; and a volume rendering unit configured to create the three-dimensional image from the intensity volume data and the illuminance volume data.

According to this configuration, it is possible to provide an ultrasound diagnostic apparatus to create a three-dimensional image that expresses the shading effect due to the leakage, absorption or others of light.

Advantageous Effects of Invention

In the present invention, the illuminance at a position corresponding to a coordinate of intensity volume data is calculated based on optical data and a weight coefficient, and illuminance volume data are created based on the calculated illuminance. Thereby, it is possible to create a three-dimensional image that expresses the shading effect due to the leakage, absorption or others of light.

BRIEF DESCRIPTION OF DRAWINGS

FIG. 14 is a diagram illustrating another example of the selection method of the color map.

DESCRIPTION OF EMBODIMENT

Figure 1:
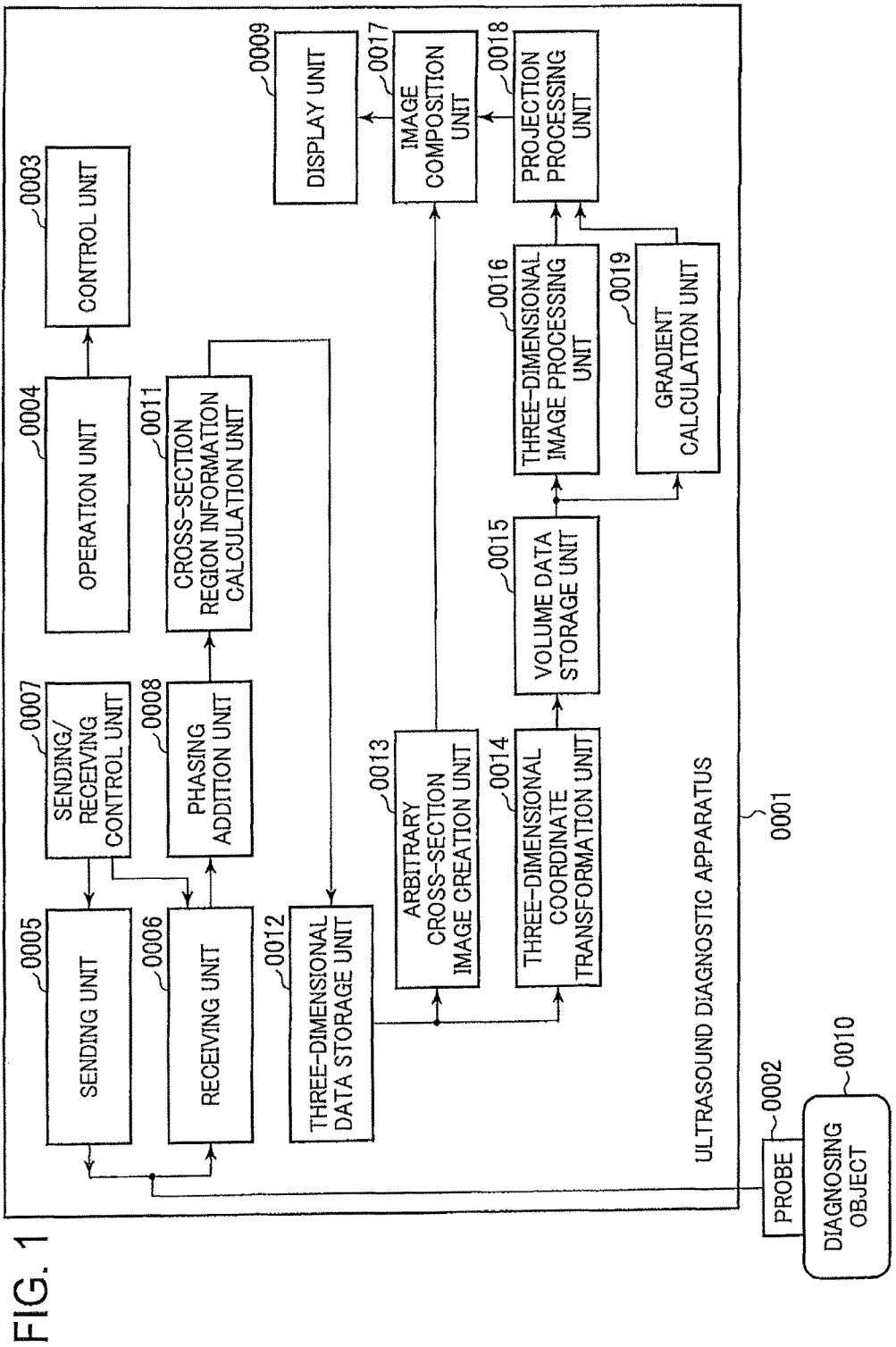
FIG. 1 is a block diagram illustrating an example of an ultrasound diagnostic apparatus according to a present embodiment.

Hereinafter, descriptions will be given of an ultrasound diagnostic apparatus of the present invention, using the drawings. FIG. 1 is a block diagram illustrating an example of an ultrasound diagnostic apparatus according to a present embodiment. As illustrated in FIG. 1, an ultrasound diagnostic apparatus 0001 includes a control unit 0003, an operation unit 0004, a sending unit 0005, a receiving unit 0006, a sending/receiving control unit 0007, a beamformer unit 0008, a display unit 0009, a multi-planar reconstruction (B-mode) region information calculation unit 0011, a three-dimensional data storage unit 0012, an arbitrary multi-planar reconstruction (B-mode) image creation unit 0013, a three-dimensional coordinate transformation unit 0014, a volume data storage unit 0015, a three-dimensional image processing unit 0016, an image composition unit 0017, a volume rendering unit 0018, and a gradient calculation unit 0019 and the ultrasound diagnostic apparatus 0001 displays a three-dimensional image of an object based on luminance volume data. Also, the ultrasound diagnostic apparatus 0001 is connected to an ultrasonic probe 0002.

The ultrasonic probe 0002 is used with being in contact with a diagnosing object 0010. The ultrasonic probe 0002 is formed of a plurality of transducers arranged therein, and has a function of sending/receiving an ultrasonic wave to/from the diagnosing object 0010 via the transducers. The ultrasonic probe 0002 is formed of the plurality of transducers having a rectangular shape or a fan-like shape, mechanically sweeps or manually moves the transducers in a direction perpendicular to an arrangement direction of the plurality of transducers, and thereby three-dimensionally sending/receiving of an ultrasonic wave is allowed. The ultrasonic probe 0002 may be an ultrasonic probe which has a plurality of transducers two-dimensionally arranged therein and can control sending/receiving of an ultrasonic wave electrically.

The control unit 0003 controls the respective components of the ultrasound diagnostic apparatus 0001 and the ultrasonic probe 0002. The operation unit 0004 conducts various inputs to the control unit 0003. The operation unit 0004 includes a keyboard, a trackball etc.

The sending unit 0005 makes the ultrasonic probe 0002 send an ultrasonic wave to the diagnosing object 0010 repeatedly at fixed time intervals. The sending unit 0005 drives the transducers of the ultrasonic probe 0002 to generate an emission pulse for generating an ultrasonic wave. The sending unit 0005 has a function of setting a convergence point of the sent ultrasonic waves at a certain depth. The receiving unit 0006 receives a reflection echo signal reflected from the diagnosing object 0010. The receiving unit 0006 amplifies a reflection echo signal received by the ultrasonic probe 0002 at a predetermined gain to generate an RF signal, i.e., a receipt signal. The sending/receiving control unit 0007 controls the sending unit 0005 and the receiving unit 0006.

The beamformer unit 0008 conducts phasing addition of the reflection echo received by the receiving unit 0006. The beamformer unit 0008 controls the phase of the RF signal amplified by the receiving unit 0006, forms an ultrasonic beam for one or plural convergence points, and generates RF signal frame data (corresponding to RAW data). The multi-planar reconstruction (B-mode) region information calculation unit 0011 forms a multi-planar reconstruction (B-mode) image based on the RF signal frame data generated by the beamformer unit 0008. The three-dimensional data storage unit 0012 stores a plurality of the multi-planar reconstruction (B-mode) images formed by the multi-planar reconstruction (B-mode) region information calculation unit 0011.

The arbitrary multi-planar reconstruction (B-mode) image creation unit 0013 creates an arbitrary multi-planar reconstruction (B-mode) image based on the acquired shapes of the multi-planar reconstruction (B-mode) images. The three-dimensional coordinate transformation unit 0014 conducts three-dimensional coordinate transformation based on the acquired shapes of the multi-planar reconstruction (B-mode) images, generates luminance volume data, and stores the luminance volume data in the volume data storage unit 0015. The three-dimensional image processing unit 0016 creates illuminance volume data with use of the luminance volume data stored in the volume data storage unit 0015.

The gradient calculation unit 0019 creates gradient volume data with use of the luminance volume data stored in the volume data storage unit 0015. The volume rendering unit 0018 conducts rendering processing with use of the illuminance volume data, the luminance volume data and the gradient volume data to generate a three-dimensional image. Also, the volume rendering unit 0018 may create a three-dimensional image from the luminance volume data and the illuminance volume data. The image composition unit 0017 composes the three-dimensional image generated by the volume rendering unit 0018 and the arbitrary multi-planar reconstruction (B-mode) image created by the arbitrary multi-planar reconstruction (B-mode) image creation unit 0013. The display unit 0009 displays an image for display created by the image composition unit 0017.

Next, description will be given of processing of three-dimensional data. At the same time of sending/receiving of an ultrasonic wave, the ultrasonic probe 0002 switches a sending/receiving direction two-dimensionally, thereby the ultrasonic probe 0002 can conduct measurement, for example, along two axes, that is, and. Based on the set condition in the control unit 0003, the multi-planar reconstruction (B-mode) region information calculation unit 0011 receives the RF signal frame data output by the beamformer unit 0008, conducts signal processing such as gain correction, log compression, wave detection, contour emphasis, and smoothing processing, and forms two-dimensional multi-planar reconstruction (B-mode) region data.

The three-dimensional data storage unit 0012 has a function of storing a plurality of the two-dimensional multi-planar reconstruction (B-mode) region data, which is data output by the multi-planar reconstruction (B-mode) region information calculation unit 0011, based on the sending/receiving direction corresponding to an acquisition point. For example, a plurality of two-dimensional multi-planar reconstruction (B-mode) images created based on the measurement result of sending/receiving time series ultrasonic data, which has been subject to sampling in a depth direction, in the direction are obtained by driving in the direction perpendicular to the direction, and a plurality of two-dimensional multi-planar reconstruction (B-mode) region data associated with are stored as three-dimensional multi-planar reconstruction (B-mode) region data.

With use of the three-dimensional multi-planar reconstruction (B-mode) region data stored in the three-dimensional data storage unit 0012, the three-dimensional coordinate transformation unit 0014 conducts three-dimensional coordinate transformation to a coordinate in a space based on the acquisition point (depth,), generates luminance volume data, and stores the generated luminance volume data in the volume data storage unit 0015.

With use of the three-dimensional multi-planar reconstruction (B-mode) region data stored in the three-dimensional data storage unit 0012, the arbitrary multi-planar reconstruction (B-mode) image creation unit 0013 creates an arbitrary multi-planar reconstruction (B-mode) image on an arbitrary plane in the three-dimensional space set by the control unit 0003 and the operation unit 0004, based on the acquisition point (depth,).

The three-dimensional image processing unit 0016 creates illuminance volume data based on the luminance volume data stored in the volume data storage unit 0015. The gradient calculation unit 0019 creates volume data in which gradients in a visual line direction at respective voxel coordinates are calculated, based on the luminance volume data stored in the volume data storage unit 0015.

Next, description will be given of processing of the three-dimensional image processing unit 0016. The three-dimensional image processing unit 0016 is a characteristic processing unit of the ultrasound diagnostic apparatus 0001 according to the present embodiment, and creates the illuminance volume data based on a light source in the three-dimensional space set by the control unit 0003 and the operation unit 0004, with use of the luminance volume data stored in the volume data storage unit 0015.

Figure 2:
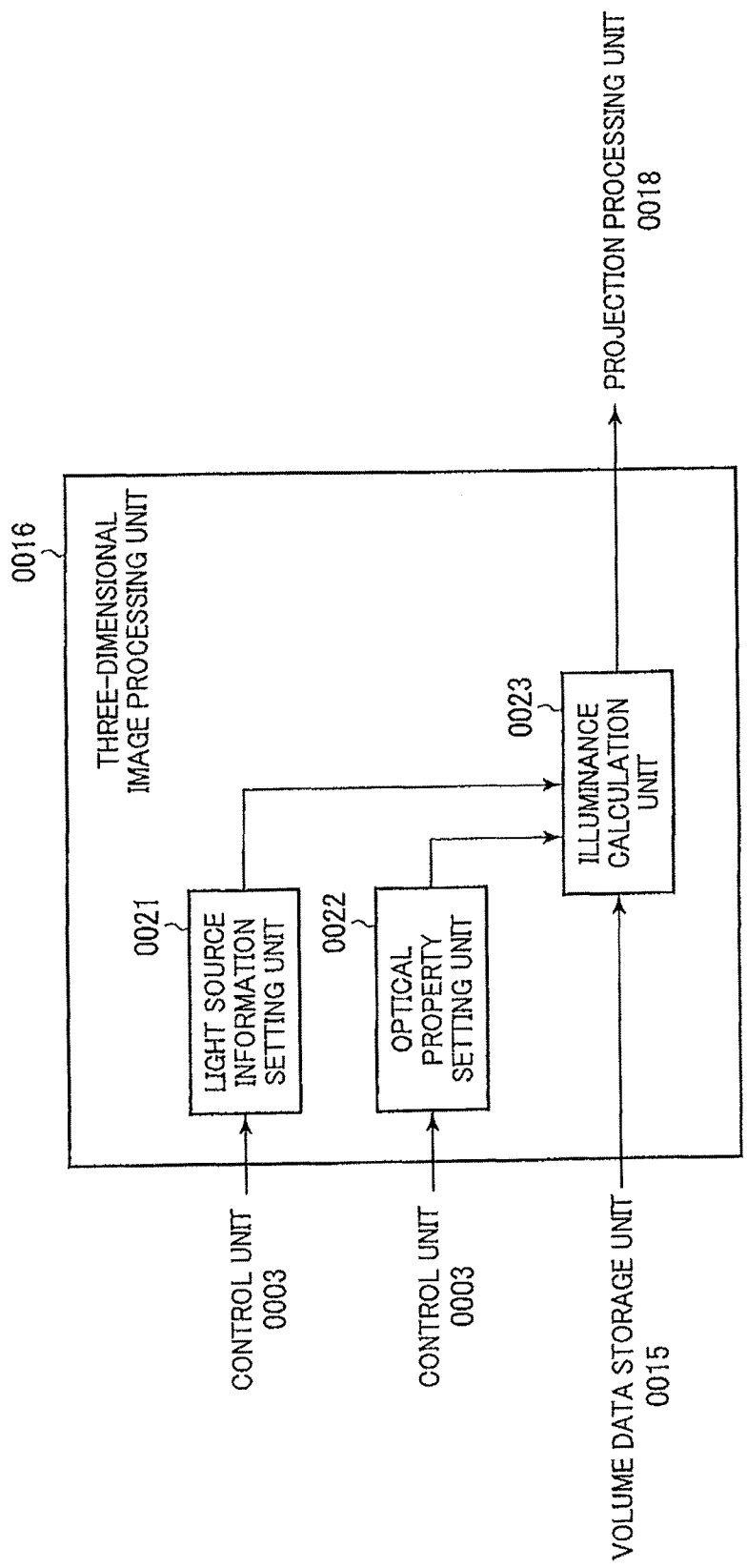
FIG. 2 is a block diagram illustrating an example of a three-dimensional image processing unit.

FIG. 2 is a block diagram illustrating an example of the three-dimensional image processing unit 0016. As illustrated in FIG. 2, the three-dimensional image processing unit 0016 includes a light source information setting unit 0021, an optical property setting unit 0022, and an illuminance calculation unit 0023. The ultrasound diagnostic apparatus 0001 according to the present embodiment is an ultrasound diagnostic apparatus 0001 to display a three-dimensional image of an object based on the luminance volume data, and includes: a light source information setting unit 0021 to set light source data indicating the property of the light source that is set in the three-dimensional space; an optical property setting unit 0022 to set a weight coefficient indicating the optical property of the luminance volume data with respect to the light source; an illuminance calculation unit 0023 to calculate the illuminance at a position corresponding to a coordinate of the luminance volume data, based on the optical data and the weight coefficient, and to create the illuminance volume data based on the calculated illuminance; and a volume rendering unit 0018 to create the three-dimensional image from the luminance volume data and the illuminance volume data. Further, an ultrasound three-dimensional image creation method according to the present embodiment is an ultrasound three-dimensional image creation method of displaying the three-dimensional image of the object based on the luminance volume data, and includes: setting the light source data indicating the property of the light source that is set in the three-dimensional space; setting the weight coefficient indicating the optical property of the luminance volume data with respect to the light source; calculating the illuminance at the position corresponding to the coordinate of the luminance volume data, based on the optical data and the weight coefficient, and creating the illuminance volume data based on the calculated illuminance; and creating the three-dimensional image from the luminance volume data and the illuminance volume data.

The light source information setting unit 0021 sets (generates) the light source data indicating the property of the light source that is set in the three-dimensional space for the three-dimensional image. For example, the light source information setting unit 0021 sets the light source data indicating intensity of the light source. The light source information setting unit 0021 can set the light source data even by adjusting at least one of the intensity of the light source, a position of the light source in a three-dimensional space, a direction of the light source, a color tone of the light source, and a shape of the light source. The optical property setting unit 0022 sets the optical property of the luminance volume data that are set by the control unit 0003 and the operation unit 0004. The optical property setting unit 0022 sets a weight coefficient indicating the optical property of luminance volume data to the light source. The illuminance calculation unit 0023 calculates the illuminance to be arranged on the luminance volume data, based on the light source data set by the light source information setting unit 0021 and the optical property set by the optical property setting unit 0022, and creates the illuminance volume data. That is, the illuminance calculation unit 0023 calculates the illuminance at a position corresponding to a coordinate of the luminance volume data, based on the optical data and the weight coefficient, and creates the illuminance volume data based on the calculated illuminance.

Next, description will be given of the light source information to be set by the light source information setting unit 0021, the optical property to be set by the optical property setting unit 0022, and a creation method of the illuminance volume data in the illuminance calculation unit 0023.

Figure 3:
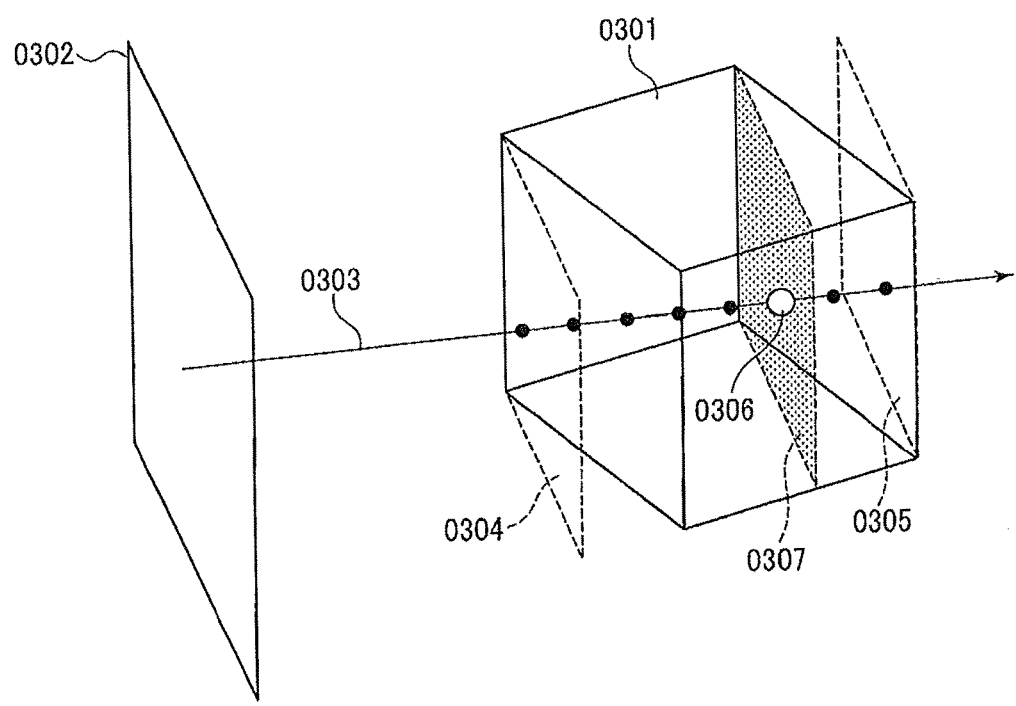
FIG. 3 is a conceptual diagram schematically illustrating intensity volume data and a positional relation of a light source.

FIG. 3 is a conceptual diagram schematically illustrating the luminance volume data and a positional relation of the light source. As shown in FIG. 3, by the control unit 0003 and the operation unit 0004, a light source (parallel light source) 0302 is set in a light source direction 0303, for the luminance volume data 0301 in the volume data storage unit 0015. The position of the light source 0302 in the three-dimensional space, the light source direction 0303, and the light source data are generated by the light source information setting unit 0021.

A plane 0304 shows an illuminance calculation starting position, which is a position of a plane on which the luminance volume data 0301 intersect (contact) with an orthogonal plane to the light source direction 0303 for the first time. A plane 0305 shows an illuminance calculation ending position, which is a position of a plane on which the luminance volume data 0301 intersect (contact) with an orthogonal plane to the light source direction 0303 for the last time.

The illuminance calculation unit 0023 conducts illuminance calculation for a plane orthogonal to the light source direction 0303 (an orthogonal plane to the light source direction 0303). In FIG. 3, the illuminance calculation unit 0023 conducts the illuminance calculation in the range from the plane 0304 to the plane 0305. For example, in the illuminance calculation of a sample 0306 positioned in the light source direction 0303, the illuminance calculation is conducted for a plane 0307.

Figure 4:
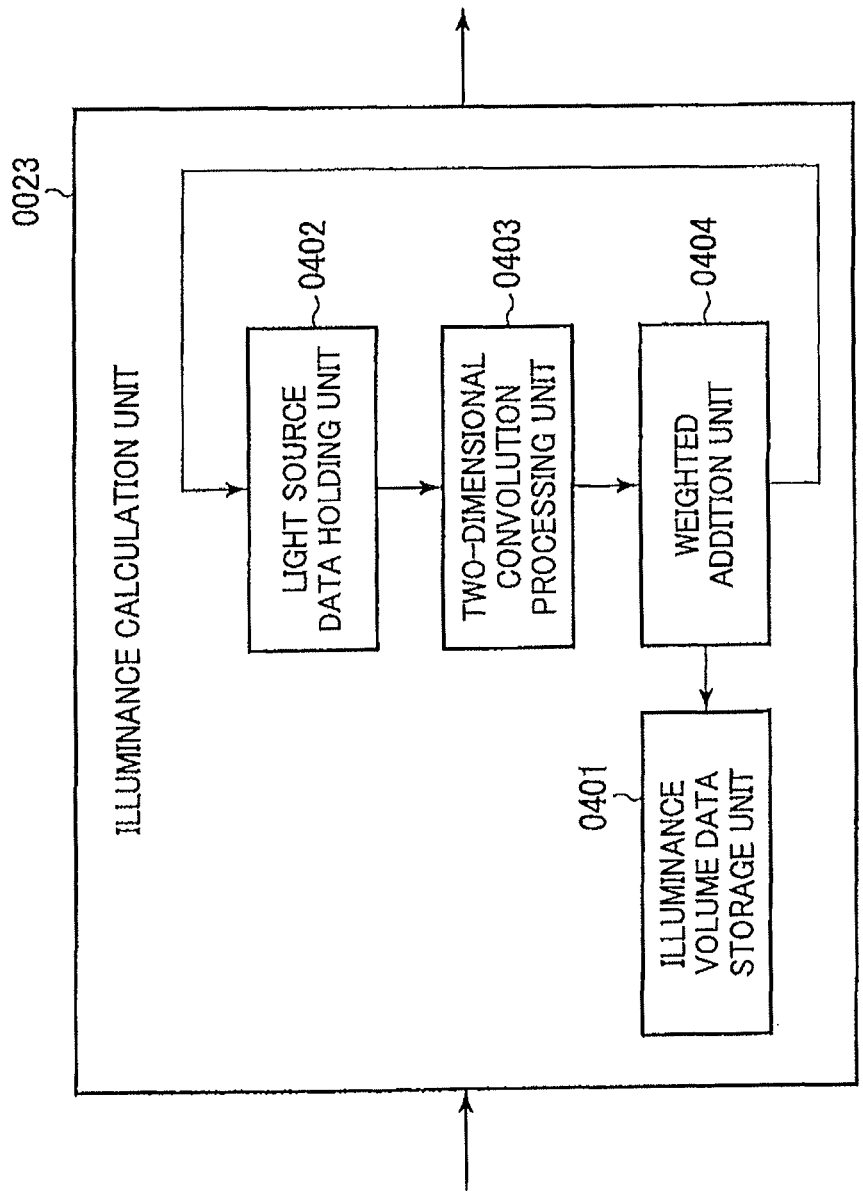
FIG. 4 is a block diagram illustrating an example of a configuration of an illuminance calculation unit.

Next, description will be given of an example of the configuration of the illuminance calculation unit 0023, using FIG. 4. As illustrated in FIG. 4, the illuminance calculation unit 0023 includes an illuminance volume data storage unit 0401, a light source data holding unit 0402, a two-dimensional convolution processing unit 0403, and a weighted addition unit 0404. The illuminance calculation unit 0023 includes the two-dimensional convolution processing unit 0403 which conducts two-dimensional convolution of the light source data, whereby generating two-dimensional convolution data, and the weighted addition unit 0404 which conducts weighted addition to the light source data and the two-dimensional convolution data based on the weight coefficient, whereby creating the illuminance volume data.

The illuminance calculation unit 0023 includes the light source data holding unit 0402 which holds, as input light source data, an initial value of the light source data and a result of the weighted addition by the weighted addition unit, and the illuminance calculation unit 0023, while switching a voxel luminance from the illuminance calculation starting position to the illuminance calculation ending position in the luminance volume data, conducts two-dimensional convolution of the input light source data, whereby generating two-dimensional convolution data, and conducts weighted addition to the input light source data and the two-dimensional convolution data based on the weight coefficient, whereby creating the illuminance volume data.

The light source data holding unit 0402 receives the light source data generated by the light source information setting unit 0021, and holds them as the initial value. Hereinafter, the light source data held by the light source data holding unit 0402 are referred to as the "input light source data". The two-dimensional convolution processing unit 0403 conducts two-dimensional convolution of the input light source data (light source data), whereby generating two-dimensional convolution data. The two-dimensional convolution process, which means the convolution on a two-dimensional plane, is a two-dimensional convolution process of the input light source data (light source data) and a convolution kernel indicating a scattering property. For example, it is conducted for the plane 0307. Further, the convolution kernel is configured by a two-dimensional matrix, and is set by the control unit.

The weighted addition unit 0404 receives two-dimensional convolution data which is an output result of the two-dimensional convolution processing unit 0403, and receives the input light source data held by the light source data holding unit 0402. The weighted addition unit 0404 conducts weighted addition to the input light source data (light source data) and the two-dimensional convolution data based on the weight coefficient, whereby generating the illuminance volume data. The weight coefficient to be used by the weighted addition unit 0404 is set by the optical property setting unit 0022, as the optical property of the luminance volume data with respect to the light source. Hereinafter, the weighted addition result to be created by the weighted addition unit 0404 is referred to as the "output illuminance data".

The output illuminance data are stored in a position corresponding to the voxel coordinate of the illuminance volume data storage unit 0401. Furthermore, the output illuminance data is input to the light source data holding unit 0402, and is stored (held) as input light source data. Specifically, the light source data holding unit 0402 holds, as the input light source data, the initial value of the light source data and the result of weighted addition by the weighted addition unit 0404.

Here, the initial value of the input light source data is the light source data set by the light source information setting unit 0021, and is input and set (held) in the light source data holding unit 0402, before the illuminance calculation unit 0023 starts the illuminance calculation.

The illuminance calculation unit 0023 (the two-dimensional convolution processing unit 0403 and the weighted addition unit 0404) generates the two-dimensional convolution data, by conducting the two-dimensional convolution of the input light source data while switching the voxel luminance from the illuminance calculation starting position (the plane 0304) to the illuminance calculation ending position (the plane 0305) in the luminance volume data, and creates the illuminance volume data, by conducting the weighted addition of the input light source data and the two-dimensional convolution data based on the weight coefficient.

Figure 5:
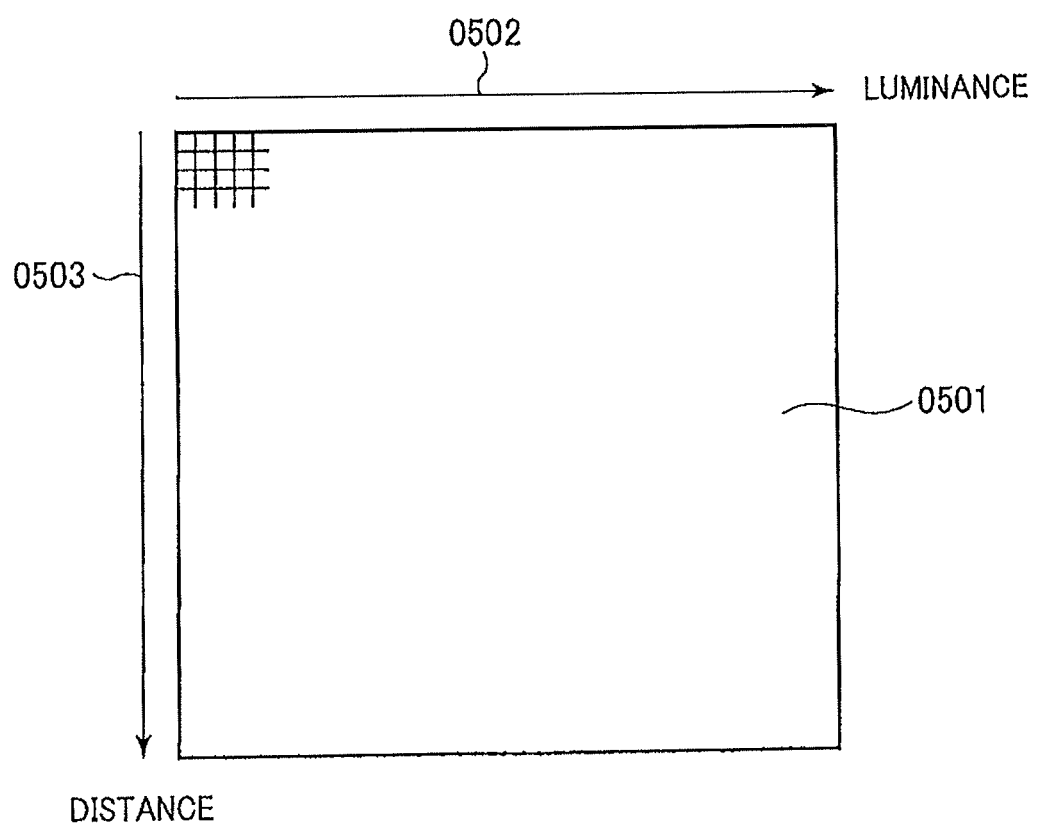
FIG. 5 is a diagram illustrating an example of a two-dimensional weight coefficient table that specifies a weight coefficient.

Next, description will be given of a method for setting of a weight coefficient used by the weighted addition unit 0404, using FIG. 5. As shown in FIG. 5, a two-dimensional weight coefficient table 0501, which includes the weight coefficient to be set by the control unit 0003, is a two-dimensional table for referring to two-dimensionally stored weight coefficients, using two indexes: the luminance of the luminance volume data and the distance from a body surface (or a tissue surface). That is, the weight coefficient is specified by the two-dimensional weight coefficient table 0501 whose indexes are the luminance of the luminance volume data and the distance from the surface of the object. In this case, the optical property setting unit 0022 sets the weight coefficient corresponding to the luminance of the luminance volume data and the distance from the surface of the object.

The optical property in the present embodiment is defined by a weight coefficient which is set so as to reproduce the behavior (action) of light, and is set by the optical property setting unit 0022, based on the optical property of the tissue. The optical property setting unit 0022 sets the two-dimensional weight coefficient table 0501 including weight coefficients, as the optical property of luminance volume data.

Description will be given of a case where there are two weight coefficients: a and b, as the weight coefficient to be referred to from the two-dimensional weight coefficient table 0501, based on the two indexes: the luminance of the luminance volume data and the distance from the body surface (or the tissue surface), as shown in FIG. 5. If a weight coefficient added to the input light source data is a and a weight coefficient added to the two-dimensional convolution data is b, adjustment of magnitude of a and b allows easy setting of the behavior of light (degree of scattering, etc.).

Also, the weight coefficients a and b and an added sum of the light source data and the two-dimensional convolution data are output to the illuminance volume data storage unit 0401. When a total value of the weight coefficients a and b is set to be large, enhanced illuminance can be set, and when the total value of the weight coefficients a and b is set to be small, attenuated illuminance can be set.

In the present embodiment, the two-dimensional weight coefficient table 0501 includes the luminance and the distance from the body surface (or the tissue surface), as two reference indexes. In the case of ultrasonic data, the luminance mirroring the acoustic impedance of a tissue can be useful information mirroring the property of a biological tissue. The luminance in ultrasonic data mirrors the amplitude of reflected waves that are obtained when radiated ultrasonic waves are reflected from a scattering body, and ordinarily, ultrasonic waves are attenuated as they are transmitted to a deep part. Therefore, in ultrasonic data, it is difficult to distinguish tissues only by the luminance. Hence, the distance from the body surface (or the tissue surface) of the object is added as an index. Thereby, it is possible to distinguish tissues in ultrasonic data.

For example, suppose that the object is an unborn child and ultrasonic waves reach an arm of the unborn child through amniotic fluid. It is well known that the ultrasonic waves reflected from the diaphysis (hard tissue) of the arm have a high luminance. However, it is well known that, although the surface of the arm is a soft tissue, the luminance at a moment when they reach the surface of the arm is a high luminance similarly to the diaphysis, because attenuation does not occur. Thus, in the case where the index is only the luminance, it is difficult to discriminate between the soft tissue and the diaphysis (hard tissue). Hence, the distance from the body surface of the object is added as an index. The diaphysis is present in the interior of the tissue of the unborn child, and therefore, by setting the property of the tissue with use of both the distance from the body surface (or the tissue surface) and the luminance, the discrimination of the tissue becomes possible.

For example, in the case where the luminance for a certain voxel is higher than a preset threshold, the judgment that the distance from the body surface (or the tissue surface) falls within the tissue is made, and a distance equivalent to one voxel is added to the value of the distance from the body surface (or the tissue surface). On the other hand, in the case where the luminance for a certain voxel is lower than the preset threshold, the judgment that it does not fall within the tissue is made, and the value of the distance from the body surface (or the tissue surface) for the voxel is initialized.

Since the distance from the body surface (or the tissue surface) is used as the index of the weight coefficient, in the case where a soft tissue with a high luminance is present on the tissue surface and a diaphysis with a similar degree of luminance to the soft tissue is present at a deep position relative to the tissue surface, such as the case of the arm of the unborn child, even if a similar degree of luminance, it is possible to give optical effects that are different depending on the tissue, by setting different weight coefficients corresponding to the distance from the body surface (or the tissue surface). That is, by discriminating between the soft tissue and the diaphysis (hard tissue) and setting different weight coefficients corresponding to the distance from the body surface (or the tissue surface), it is possible to express the behavior of light (leakage, absorption, scattering, reflection, or the like) in the tissue while discriminating between the soft tissue and the diaphysis (hard tissue), and to obtain an image in which reality is improved in the volume rendering method. By using a characteristic weight coefficient corresponding to the property of the tissue, it is possible to give an appropriate optical effect, even in the case where it is difficult to specify the property (or the type) of the tissue from only the luminance value, such as the case of ultrasonic data.

Thus, without complicated calculation, a two-dimensional weight coefficient table reflecting properties of a tissue is set, a behavior of light (degree of scattering, etc.) is adjusted based on the two-dimensional weight coefficient table, and thereby it is possible to give an optical effect in the tissue easily and arbitrarily, and the three-dimensional image in which reality is improved depending on a property of the tissue (for example, hardness of the tissue) can be created.

While switching the voxel luminance referred to by the weighted addition unit 0404 from the illuminance calculation starting position (the plane 0304) to the illuminance calculation ending position (the plane 0305), the illuminance calculation unit 0023 repeats the aforementioned illuminance calculation processing.

After calculation to the illuminance calculation ending point is finished, the illuminance calculation unit 0023 creates the illuminance volume data in which illuminance to be arranged on the luminance volume data is calculated, and the illuminance volume data is stored in the illuminance volume data storage unit 0401.

A behavior property of light varies depending on wavelengths of a light source based on the law of nature. Accordingly, if reality is to be improved based on the law of nature, illuminance calculation is conducted for each wavelength of the light source. In this case, a weight coefficient varies for each wavelength of the light source.

The light source information setting unit 0021 sets light source data corresponding to a plurality of wavelengths of the light source. The optical property setting unit 0022 sets a weight coefficient for each of the plurality of wavelengths.

The illuminance calculation unit 0023 conducts illuminance calculation for each wavelength of the light source 0302 to generate a plurality of illuminance volume data each for the wavelength. For example, if the light source 0302 has seven colors of visible rays, the illuminance calculation unit 0023 sets seven types of weight coefficient (or two-dimensional weight coefficient table) and generates seven types of illuminance volume data. Furthermore, if the light source 0302 has three primary colors of additive color mixture, the illuminance calculation unit 0023 sets three types of weight coefficient (or two-dimensional weight coefficient table) corresponding to wavelengths of elements R, G, B, and generates three types of illuminance volume data. That is, the light source information setting unit 0021 sets the light source data corresponding to the plurality of wavelengths of the light source, the optical property setting unit 0022 sets the weight coefficient for each of the plurality of wavelengths, and the illuminance calculation unit 0023 creates the illuminance volume data for each of the plurality of wavelengths.

In the present embodiment, description will be given of a case where the light source 0302 has three primary colors of additive color mixture, three types of weight coefficient (or two-dimensional weight coefficient table) are set, and three types of illuminance volume data are generated. The initial value of the light source data is set for each of the wavelengths of the light source 0302. That is, initial values of the light source data whose number is the same as the number of valid wavelengths are each set by the light source information setting unit 0021. Therefore, in the present embodiment, three types of light source data corresponding to the wavelengths of the R element, G element and B element are set, and are held by the light source data holding unit 0402, as input light source data that are independent of each other. Further, the initial values of the three types of light source data may be initial values to be selected through the operation unit 0004 by an operator, or may be initial values to be set with use of an image.

The illuminance calculation unit 0023 calculates the illuminance to be arranged on the luminance volume data, based on the three types of light source data and the three types of optical properties (the weight coefficient or the two-dimensional weight coefficient table), and creates the three types of illuminance volume data.

The volume rendering unit 0018 creates a three-dimensional image, based on the opacity to be referred to by the illuminance of the illuminance volume data and the luminance of the luminance volume data. In the case where the light source 0302 has the three primary colors, the volume rendering unit 0018 creates the three-dimensional image, from the three types of illuminance volume data created by the illuminance calculation unit 0023 and the luminance volume data stored in the volume data storage unit 0015. As shown in the following Equations (1) to (3), in the projection process by the volume rendering unit 0018, the three-dimensional image is generated based on the illuminance (voxel value) of the illuminance volume data L_r[k], L_g[k], L_b[k] for each of the wavelengths (R element, G element, B element), the luminance (voxel value) C of the luminance volume data, an opacity table to be referred to by the luminance C, and gradient volume data S[k]. That is, the voxel values of the illuminance volume data L_r[k], L_g[k], L_b[k] for each of the wavelengths are multiplied by opacity terms, which are obtained by the opacity table to be referred to by the luminance C of the luminance volume data, and the values of the gradient volume data S[k], and are accumulated in the visual line direction. Thereby, the three-dimensional image is generated. In the equations, "k" represents the voxel coordinate in the visual line direction. The visual line direction is set as a direction for observing an ultrasound image by the operation unit 0004 via the control unit 0003.

$$\mathrm{OUT\_}R[K] = ^{k=0:K}((L\_r[k])[C[k]]^{m=0:k-1}(1-[C[m]])) \quad (1)$$

$$\mathrm{OUT\_}G[K] = ^{k=0:K}((L\_g[k])[C[k]]^{m=0:k-1}(1-[C[m]])) \quad (2)$$

$$\mathrm{OUT\_}B[K] = ^{k=0:K}((L\_b[k])[C[k]]^{m=0:k-1}(1-[C[m]])) \quad (3)$$

The three-dimensional image created by the three-dimensional image processing unit 0016 is arranged on the same screen as an arbitrary multi-planar reconstruction (B-mode) image by the image composition unit 0017, and is displayed by the display unit 0009.

Here, in the present embodiment, the ultrasound diagnostic apparatus 0001 includes the gradient calculation unit 0019, but can exclude the gradient calculation unit 0019. In this case, the term of the gradient volume data S[k] in Equations (1) to (3) does not contribute to the three-dimensional image to be created, because of being excluded from Equations (1) to (3) (or, because of being dealt with as "1.0").

Figure 6:
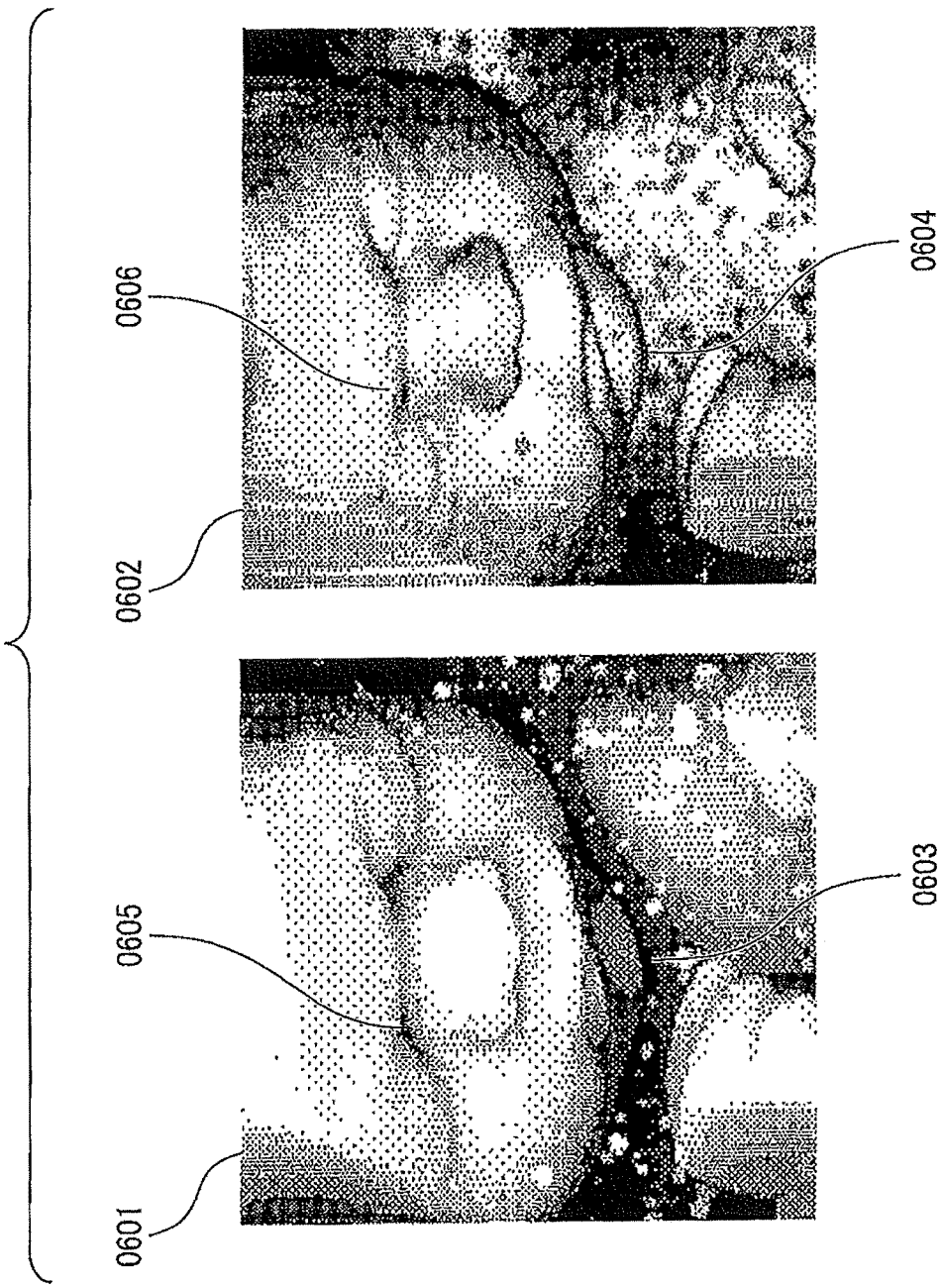
FIG. 6 is a diagram for explaining characteristics of a three-dimensional image according to the present embodiment.

Next, description will be given of a characteristic of the three-dimensional image according to the present embodiment, using FIG. 6. A three-dimensional image 0601 in FIG. 6 is a three-dimensional image configured by the technique according to the present embodiment, and a three-dimensional image 0602 is a three-dimensional image configured by a general volume rendering technique, which is typified by the Levoy technique. As shown in FIG. 6, the conventional three-dimensional image 0602 has a dark and thin shade 0604 along the contour of the face of an unborn child. On the other hand, in the three-dimensional image 0601 according to the present embodiment, a shade 0603 is emphasized relative to the contour of the face, and thereby the contour emerges so that the border is clear. Further, in the conventional three-dimensional image 0602, an inner canthus of the unborn child is shown by a thin contour line 0606. On the other hand, in the three-dimensional image 0601 according to the present embodiment, the inner canthus of the unborn child is displayed so as to be emphasized by a deep shade 0605, and thereby, the border is clear. Thus, it is possible to obtain a natural image in which the border is clear by the emphasis of the shade and in which reality is improved in the volume rendering method.

Figure 7:
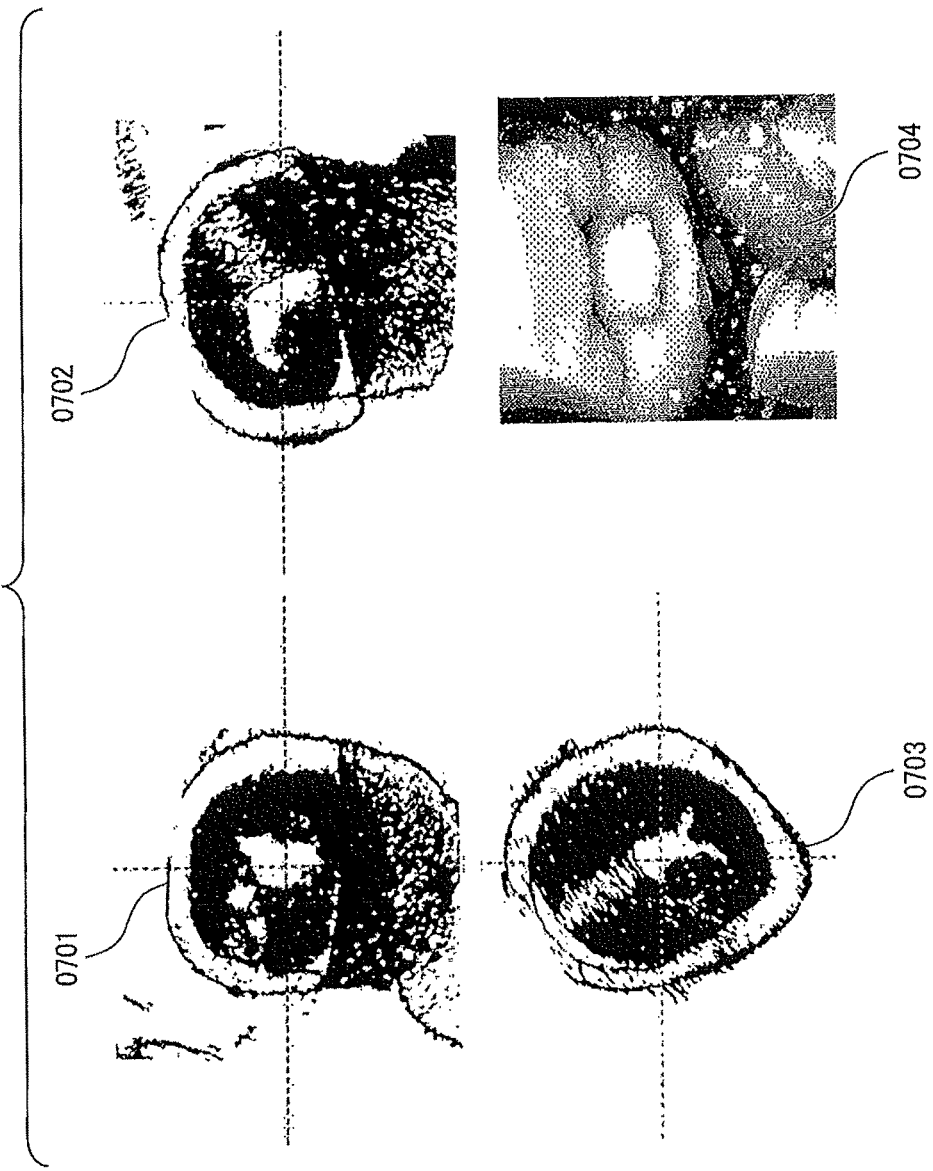
FIG. 7 is a diagram illustrating a display example in the present embodiment.

FIG. 7 is a diagram illustrating a display example according to the present embodiment. As shown in FIG. 7, three cross sections 0701, 0702, 0703 whose respective planes are orthogonal to each other, and a three-dimensional image 0704 are concurrently displayed. Thus, the three-dimensional image created by the three-dimensional image processing unit 0016 is arranged on the same screen as the three orthogonal cross sections (or arbitrary multi-planar reconstruction (B-mode) images) 0701, 0702, 0703, by the image composition unit 0017, and is displayed by the display unit 0009. By observing the surface with the three-dimensional image while referring to the respective cross sections, it is possible to improve the inspection accuracy and efficiency.

Here, other than the display format in FIG. 7, it is also possible that the superimposition between the conventional three-dimensional image 0602 and the three-dimensional image 0601 according to the present embodiment is displayed. Also, it is possible that plural pieces of light source information (light source data), plural pieces of visual line information, and three-dimensional images at a plurality of positions are concurrently displayed.

The present embodiment has been described so far, but the present invention is not limited to the present embodiment, and modification and change within the range set forth in the claims are possible.

Figure 8:
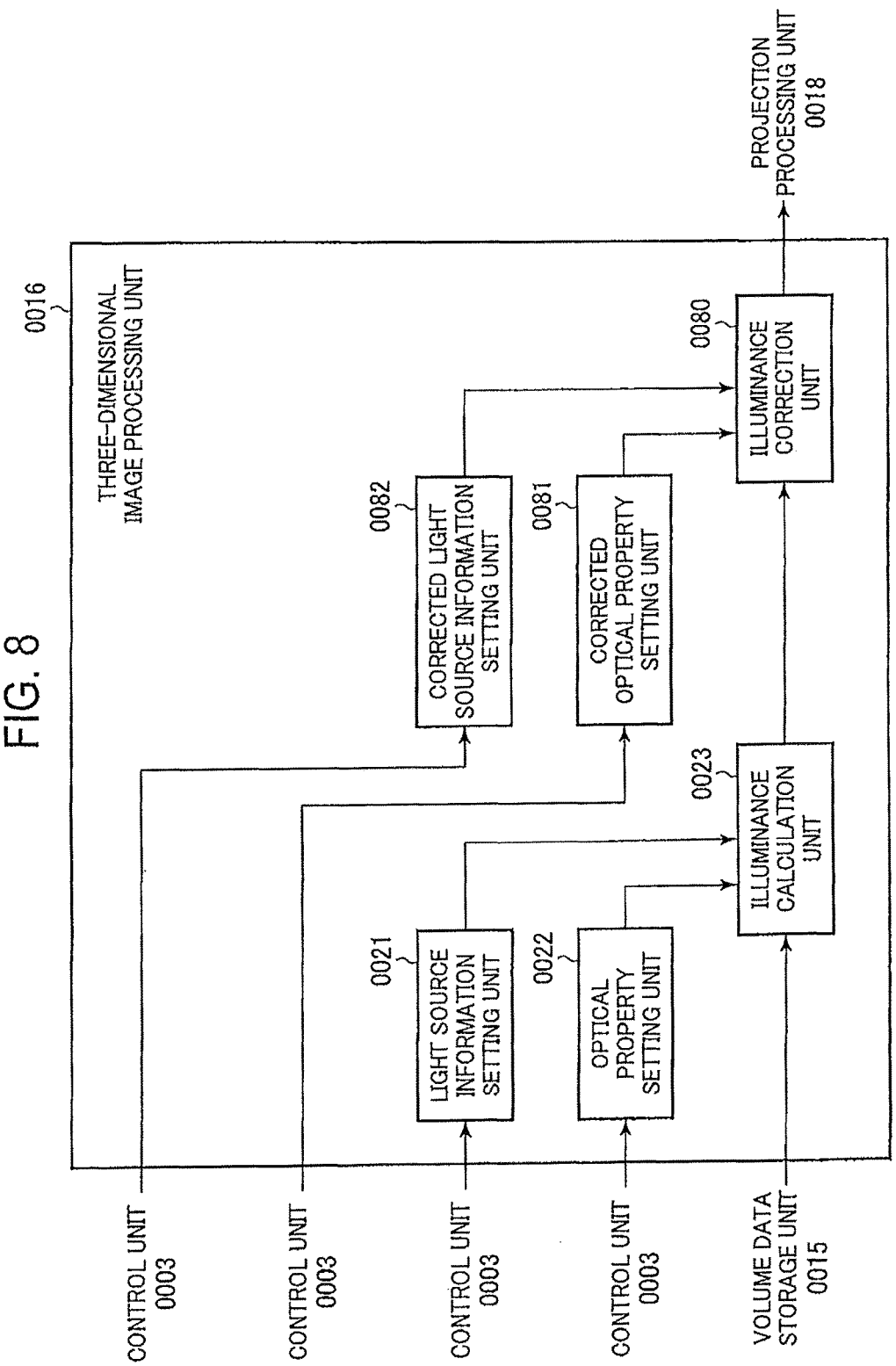
FIG. 8 is a block diagram illustrating a three-dimensional image processing unit according to a modification example of the present embodiment.
Figure 9:
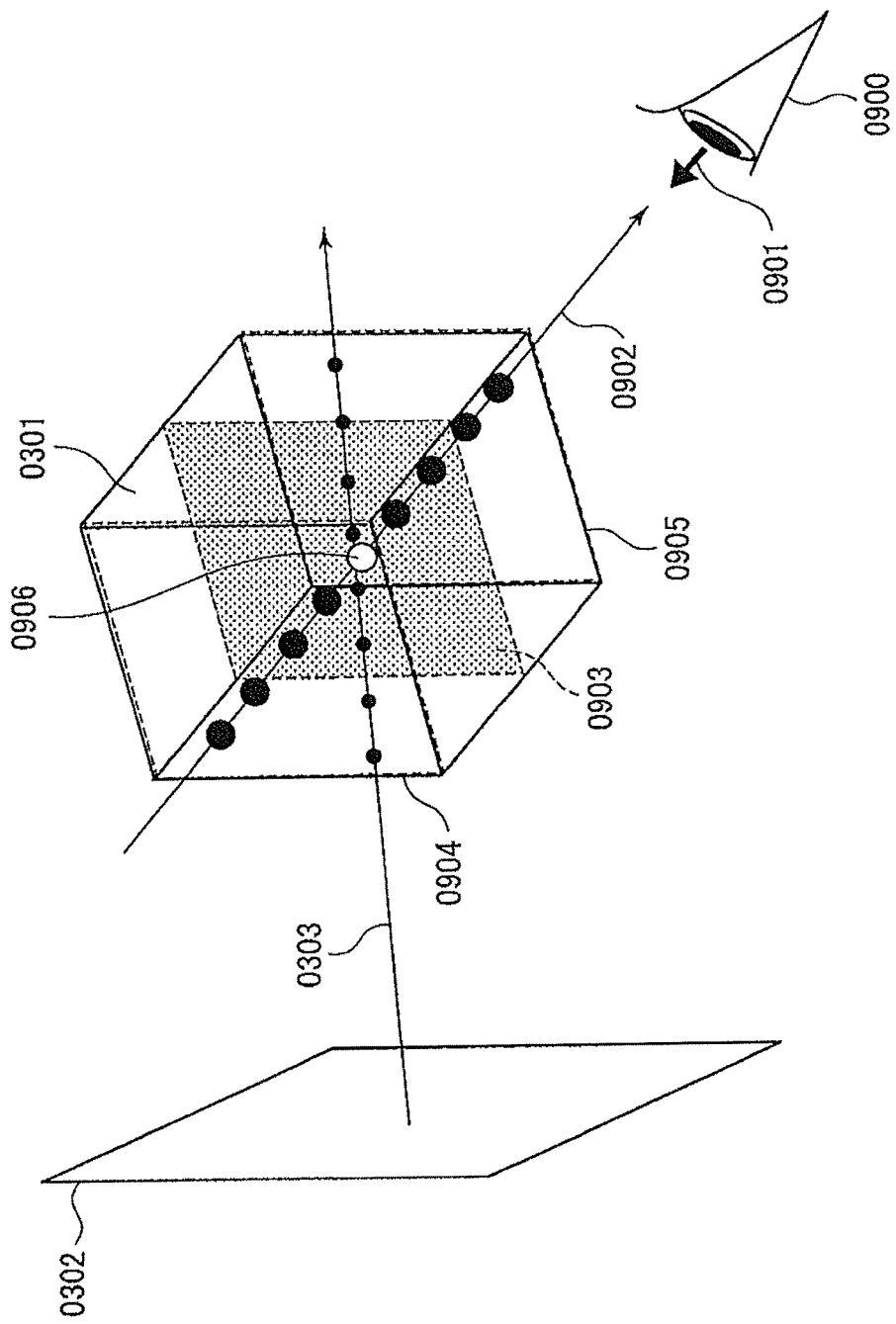
FIG. 9 is a diagram showing a conceptual diagram of an illuminance calculation according to the modification example of the present embodiment.

FIG. 8 is a block diagram illustrating a modification example of the present embodiment. FIG. 9 is a diagram showing a conceptual diagram illustrating an illuminance calculation according to the modification example of the present embodiment. As shown in FIG. 8, the ultrasound diagnostic apparatus 0001 may include an illuminance correction unit 0080, a corrected optical property setting unit 0081 and a corrected light source information setting unit 0082, at subsequent stages of the illuminance calculation unit 0023. The ultrasound diagnostic apparatus 0001 according to the present embodiment includes: the corrected light source information setting unit 0082 to set the opposite direction to the visual line direction in the three-dimensional space, as a corrected light source direction, and to set corrected light source data indicating the property of a corrected light source that emits light in the corrected light source direction; the corrected optical property setting unit 0081 to set a weight coefficient indicating the optical property of the luminance volume data with respect to the corrected light source; and the illuminance correction unit 0080 to calculate the illuminance at a position corresponding to a coordinate of the luminance volume data, based on the corrected light source data and the weight coefficient, and to create corrected illuminance volume data based on the calculated corrected illuminance, and the volume rendering unit 0018 creates the three-dimensional image from the luminance volume data and the corrected illuminance volume data.

In the illuminance volume data by the illuminance calculation unit 0023, the arrangement of the intensity of light is calculated in the direction from the near side to the far side with respect to the light source 0302. On the other hand, according to the modification example shown in FIG. 8 and FIG. 9, it is possible to add the resulting illuminance when light is transmitted in the direction from the far side to the near side with respect to a visual line direction 0901 of an observer, to the illuminance to be observed from the viewpoint 0900 of the observer.

The corrected light source information setting unit 0082 sets the corrected light source on the opposite side to the viewpoint 0900, and sets the corrected light source direction 0902 to the opposite direction to the visual line direction 0901. That is, the corrected light source information setting unit 0082 sets the opposite direction to the visual line direction 0901 in the three-dimensional space, as the corrected light source direction 0902, and sets the corrected light source data indicating the property of the corrected light source that emits light in the corrected light source direction 0902.

The corrected optical property setting unit 0081 sets the weight coefficient in the opposite direction to the visual line direction 0901 (in the corrected light source direction 0902). That is, the corrected optical property setting unit 0081 sets the weight coefficient indicating the optical property of the luminance volume data with respect to the corrected light source.

The illuminance correction unit 0080 conducts illuminance correction calculation, in order to create the corrected illuminance volume data in which the illuminance volume data have been corrected, in the direction from the far side to the near side with respect to the visual line direction. That is, the illuminance correction unit 0080 calculates the illuminance at a position corresponding to a coordinate of the luminance volume data, based on the corrected light source data and the weight coefficient, and creates the corrected illuminance volume data based on the calculated corrected illuminance.

As shown in FIG. 9, similarly to FIG. 3, the light source 0302 and the light source direction 0303 are set for the luminance volume data 0301. In the case where the visual line direction 0901 is set in the creation of the illuminance volume data, the corrected light source information setting unit 0082 sets the corrected light source on the opposite side of the viewpoint 0900, and sets the corrected light source direction 0902 to the direction opposite to the visual line direction.

A plane 0904, which is at a position of a plane on which the luminance volume data 0301 intersect (contact) with an orthogonal plane to the corrected light source direction 0902 for the first time, is a plane containing the first voxel in the corrected light source direction 0902, and shows an illuminance calculation starting position. A plane 0905, which is at a position of a plane on which the luminance volume data 0301 intersect (contact) with an orthogonal plane to the corrected light source direction 0902 for the last time, is a plane containing the last voxel in the corrected light source direction 0902, and shows an illuminance calculation ending position.

The illuminance correction unit 0080 conducts the illuminance correction for a plane orthogonal to the light source direction 0902. As shown in FIG. 9, the illuminance correction unit 0080 conducts the illuminance correction in the range from the plane 0904 to the plane 0905. For example, in the illuminance correction of a sample 0906 positioned in the corrected light source direction 0902, the illuminance correction calculation is conducted for a plane 0903.

Figure 10:
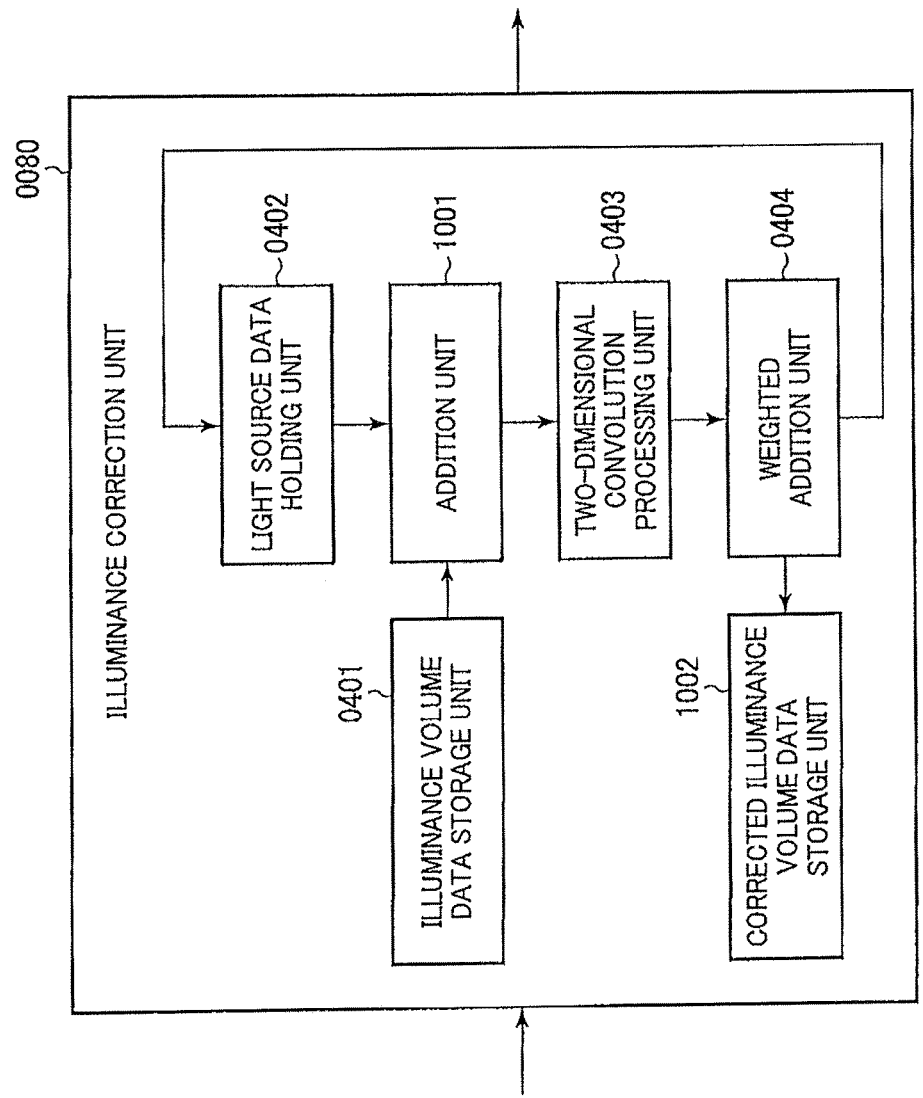
FIG. 10 is a block diagram illustrating an example of the configuration of an illuminance correction unit.

Next, description will be given of a configuration of the illuminance correction unit 0080, using FIG. 10. As shown in FIG. 10, the illuminance correction unit 0080 includes an addition unit 1001, a corrected illuminance volume data storage unit 1002, an illuminance volume data storage unit 0401, a light source data holding unit 0402, a two-dimensional convolution processing unit 0403, and a weighted addition unit 0404. Components denoted by the same reference number between FIG. 4 and FIG. 10 have the same function, unless a particular mention is made.

The illuminance correction unit 0080 includes: the addition unit 1001 to add the corrected light source data and the illuminance volume data; the two-dimensional convolution processing unit 0403 to generate two-dimensional convolution data, by conducting the two-dimensional convolution of the added value of the corrected light source data and the illuminance volume data; and the weighted addition unit 0404 to create the corrected illuminance volume data, by conducting the weighted addition of the corrected light source data and the two-dimensional convolution data based on the weight coefficient.

For the input light source data (corrected light source data) stored in the light source data holding unit 0402, the illuminance correction unit 0080 reads the output illuminance data for the corresponding coordinate, from the illuminance volume data storage unit 0401, and adds the output illuminance data to the input light source data (corrected light source data). That is, the addition unit 1001 adds the corrected light source data and the illuminance volume data. However, the light source data holding unit 0402 of the illuminance correction unit 0080 has no initial value, and in this respect, is different from the light source data holding unit 0402 of the illuminance calculation unit 0023.

In the illuminance correction unit 0080, the addition unit 1001 adds the input light source data stored in the light source data holding unit 0402 and the output illuminance data for the corresponding coordinate read from the illuminance volume data storage unit 0401, and updates the input light source data to hold them.

The two-dimensional convolution processing unit 0403 conducts the two-dimensional convolution of the input light source data held by the addition unit 1001. That is, the two-dimensional convolution processing unit 0403 conducts the two-dimensional convolution of the added value of the corrected light source data and the illuminance volume data stored in the illuminance volume data storage unit 0401, and thereby, generates the two-dimensional convolution data.

The weighted addition unit 0404 receives the two-dimensional convolution data, which are the output result of the two-dimensional convolution processing unit 0403, and receives the updated input light source data held by the addition unit 1001. The weighted addition unit 0404 conducts the weighted addition of the output result of the two-dimensional convolution processing unit 0403 and the updated input light source data held by the addition unit 1001. That is, the weighted addition unit 0404 conducts the weighted addition of the corrected light source data and the two-dimensional convolution data, based on the weight coefficient, and thereby, creates the corrected illuminance volume data. Here, the weight coefficient to be used by the weighted addition unit 0404 is set by the corrected optical property setting unit 0081 in which the setting for the correction has been conducted. As described above, the weight coefficient may be referred to from a two-dimensional table that is two-dimensionally expressed using the two indexes: the luminance of the luminance volume data and the distance from the body surface (or the tissue surface).

In the corrected illuminance volume data storage unit 1002, the result of the weighted addition unit 0404 is stored together with the positional information corresponding to the voxel coordinate. Further, the result of the weighted addition unit 0404 is input to the light source data holding unit 0402, and is stored (held) as the input light source data.

According to the modification example shown in FIG. 8 to FIG. 10, it is possible to add the resulting illuminance when light is transmitted in the direction from the far side to the near side with respect to the visual line direction 0901 of the observer, to the illuminance to be observed from the viewpoint 0900 of the observer, and it is possible to create the corrected illuminance volume data in which the illuminances in the two directions of the light source direction 0303 and the corrected light source direction 0902 have been calculated. Here, although the configuration in which the corrected illuminance volume data storage unit 1002 and the illuminance volume data storage unit 0401 are independent has been adopted, a configuration in which a common memory region is used is also possible.

Further, similarly to the present embodiment described above, for the corrected illuminance volume data created by the illuminance correction unit 0080, the illuminance calculation (or the illuminance correction calculation) may be conducted for each of the wavelengths of the light source, in order to further improve reality. In this case, similarly to the present embodiment, the illuminance calculation (or the illuminance correction calculation) is repeatedly conducted for each of the set wavelengths, and the corrected illuminance volume data for each of the set wavelengths are created. For example, in the case where the light source 0302 has the three primary colors of additive color mixture, the illuminance correction unit 0080 sets three types of weight coefficients (or two-dimensional weight coefficient tables) corresponding to the wavelengths of the R element, G element and B element, and generates three types of corrected illuminance volume data. Then, the volume rendering unit 0018 creates the three-dimensional image from the three types of corrected illuminance volume data created by the illuminance correction unit 0080 and the luminance volume data stored in the volume data storage unit 0015. That is, the volume rendering unit 0018 creates the three-dimensional image from the luminance volume data and the corrected illuminance volume data.

Thus, by calculating the illuminances from the two directions of the light source direction 0303 and the corrected light source direction 0902, it is possible to calculate the illuminance based on a more natural shade, and to create a three-dimensional image in which reality is improved, in the volume rendering method.

Figure 11:
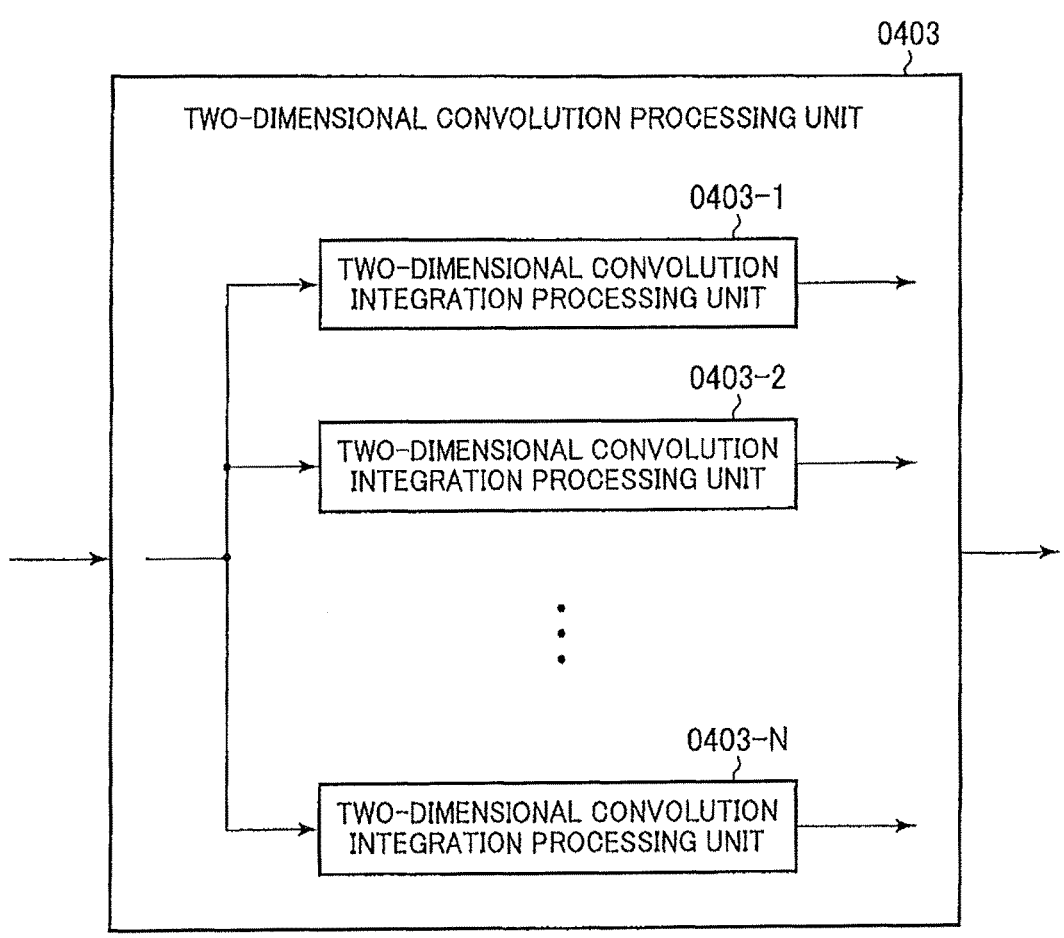
FIG. 11 is a block diagram illustrating a two-dimensional convolution processing unit according to another modification example of the present embodiment.

Also, description will be given of another modification example of the present embodiment, using FIG. 11. As shown in FIG. 11, in the other modification example, a two-dimensional convolution processing unit 0403 has a characteristic structure. Therefore, the two-dimensional convolution processing unit 0403 will be mainly described.

As shown in FIG. 11, in the illuminance calculation unit 0023, the two-dimensional convolution processing unit 0403 reads the input light source data from the light source data holding unit 0402, conducts the two-dimensional convolution process, and outputs the two-dimensional convolution data to the weighted addition unit 0404. The two-dimensional convolution processing unit 0403 generates a plurality of two or more two-dimensional convolution data. That is, the two-dimensional convolution processing unit 0403 generates the plurality of two-dimensional convolution data, by conducting a plurality of two-dimensional convolution for the light source data.

The weighted addition unit 0404 conducts the weighted addition process for the input light source data read from the light source data holding unit 0402 and the plurality of two-dimensional convolution data generated by the two-dimensional convolution processing unit 0403, creates the output illuminance data, and stores them in the corresponding voxel coordinate of the illuminance volume data storage unit 0401.

Description will be given of the configuration of the two-dimensional convolution processing unit 0403 shown in FIG. 11. The two-dimensional convolution processing unit 0403 includes two or more two-dimensional convolution processing units. The two-dimensional convolution processing units 0403-1 to 0403-N, each output different two-dimensional convolution data for the input light source data received, and each output the different two-dimensional convolume data to the weighted addition unit 0404. In this case, the weighted addition unit 0404 holds, as the weight coefficient, coefficients for the input light source data and the plurality of two-dimensional convolume data created by the two-dimensional convolution processing units 0403 (0403-1 to 0403-N). For each output result of the two-dimensional convolution processing units 0403 (0403-1 to 0403-N), a different weight coefficient may be referred to from the two-dimensional table, and be used in the weighted addition unit 0404.

Since the ultrasound diagnostic apparatus 0001 includes the plurality of two-dimensional convolution processing units 0403-1 to 0403-N in this way, it is possible to express a plurality of shading effects corresponding to the behavior of light, and to create a three-dimensional image in which the luminance has been calculated based on a more natural behavior (for example, scattering) of light, in the volume rendering method.

Figure 12:
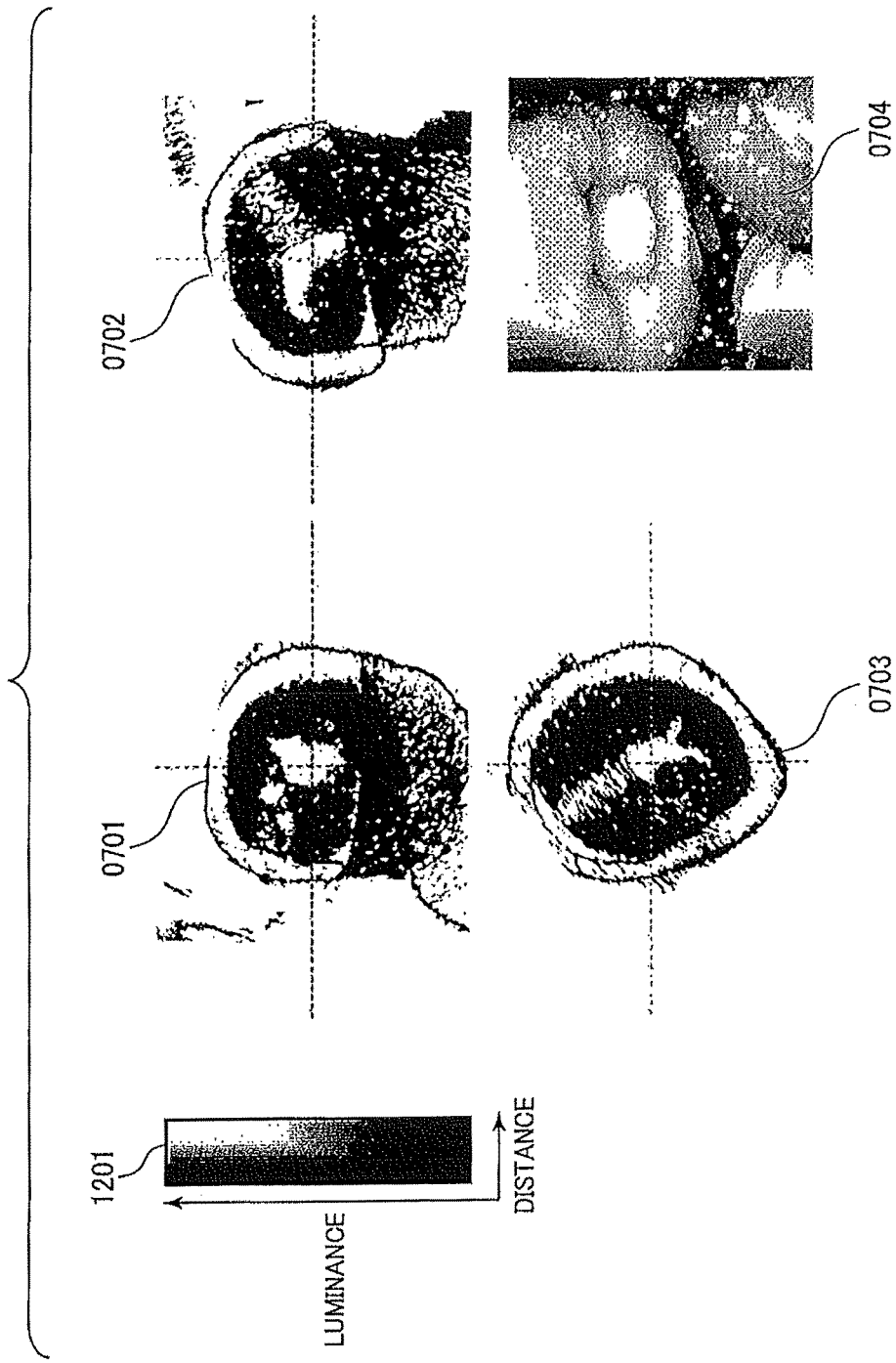
FIG. 12 is a diagram for showing that a display unit displays a color map.

Further, the display unit 0009 may display a color map indicating a color phase that is obtained from the luminance and the distance from the body surface. That is, the display unit 0009 displays a color map that corresponds to the two-dimensional weight coefficient table specifying the weight coefficient and whose indexes are the luminance of the luminance volume data and the distance from the surface of the object. FIG. 12 is a diagram for showing that the color map is displayed in a display example according to the present embodiment. As shown in FIG. 12, three cross sections 0701 to 0704 orthogonal to each other, a three-dimensional image 0704 are concurrently displayed, similarly to FIG. 7. Then, a color map 1201 is displayed. The color map 1201 is a pseudo color map for visually recognizing the tint of the three-dimensional image that is realized by the two-dimensional weight coefficient table 0501.

In the color map 1201, the luminance voxel value is arranged on the vertical axis. In the color map 1201, the repeat count (comparable to the distance from the tissue surface) of the illuminance calculation, which is conducted depending on the distance from the tissue surface and based on the two-dimensional weight coefficient table 0501 as described using FIG. 4 and FIG. 5, is arranged on the horizontal axis. Thus, the color map 1201 is a reference image indicating the color phase that is obtained from the luminance and the distance from the body surface.

By checking the color map 1201, an operator can recognize what color phase is assigned to the three-dimensional image (illumination three-dimensional image) 0704. For example, it is possible to recognize whether a displayed region shows a bone or a soft tissue. The transposition of the axis direction of the color map 1201, or the inversion of the axis is also possible.

Figure 13:
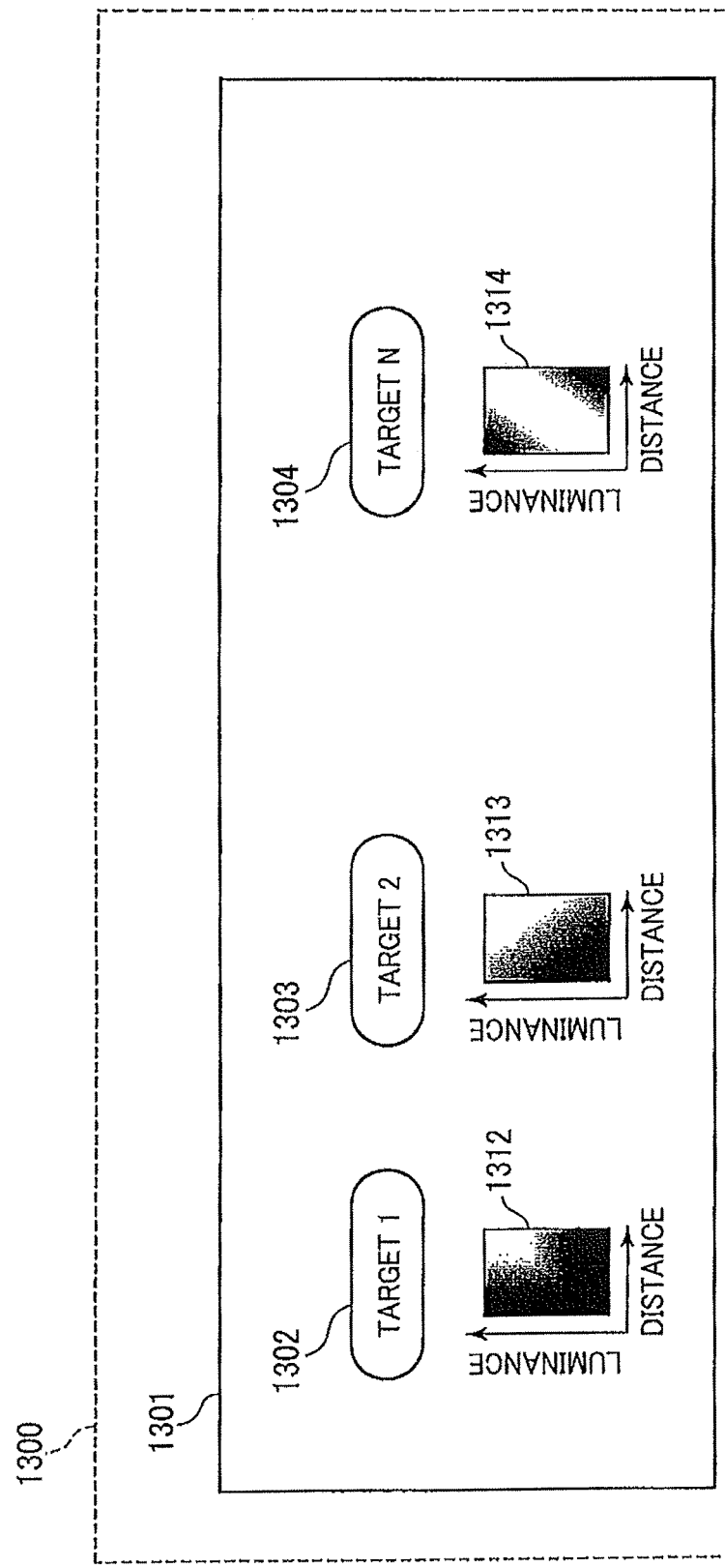
FIG. 13 is a diagram illustrating an example of the selection method of the color map.

Further, the color map 1201 may be selected from a plurality of color maps. For example, the display unit 0009 may selectively display a plurality of color maps corresponding to a plurality of two-dimensional weight coefficient tables each of which specifies the weight coefficient corresponding to the tissue of the object (the face region, bone region or others of an unborn child). FIG. 13 is a diagram illustrating a selection method of the color map

1201. As shown in FIG. 13, a graphical interface 1300 for region selection displayed on the display unit 0009 is operated by the operation unit 0004 (a pointer, a trackball, an encoder, or the like), and thereby, the color map 1201 can be selected.

A selection screen 1301 in FIG. 13 is an example of buttons to be displayed at the time of inspection, and a button corresponding to a target can be selected. For example, a button corresponding to a target is selected from a target 1 button 1302, a target 2 button 1303 a target N button 1304, and thereby, a three-dimensional image corresponding to the target can be created.

In the case where the target 1 button 1302 designates the face of the unborn child, once the target 1 button 1302 is selected, a weight coefficient (a two-dimensional weight coefficient table 0501) appropriate for the face of the unborn child is selected, this is set in the optical property setting unit 0022 or the corrected optical property setting unit 0081, and a color map 1312 corresponding to the target 1 button 1302 is displayed.

In the case where the target 2 button 1303 designates the bone of the unborn child, once the target 2 button 1303 is selected, a weight coefficient (a two-dimensional weight coefficient table 0501) appropriate for the bone region is selected, this is set in the optical property setting unit 0022 or the corrected optical property setting unit 0081, and a color map 1313 corresponding to the target 2 button 1303 is displayed. It is also possible that color maps 1312 to 1314 to be selected are displayed on the graphical interface 1300 for region selection.

The color maps 1312 to 1314 are color maps created based on the two-dimensional weight coefficient tables 0501 that are selected by the respective target buttons 1302 to 1304, and by the concurrent display with the target buttons 1302 to 1304, the operator can select an appropriate color map without a doubt.

Further, as shown in FIG. 14, a selection screen 1305 may be displayed on the graphical interface 1300 for region selection. The selection screen 1305, which is a different example of the buttons to be displayed at the time of inspection, includes a target display region 1306 to display the name of a selected target, a target selection up-button 1307, and a target selection down-button 1308, and allows a plurality of previously prepared targets to be switched with use of the target selection up-button 1307 and the target selection down-button 1308. Therefore, the operator operates the target selection up-button 1307 or the target selection down-button 1308, and thereby, a three-dimensional image corresponding to the target can be created. For example, in the case where the target 1 (target 1 button) designates the face of the unborn child and the target 2 (target 2 button) designates the bone of the unborn child, the target is switched in turns by the target selection up-button 1307 or the target selection down-button 1308. In this case, when the target 1 (target 1 button) is selected, a weight coefficient appropriate for the face of the unborn child is selected, this is set in the optical property setting unit 0022 or the corrected optical property setting unit 0081, and the color map 1201 is switched. Next, when the target 2 (target 2 button) is selected by the target selection down-button 1308, a weight coefficient appropriate for the bone region is selected, this is set in the optical property setting unit 0022 or the corrected optical property setting unit 0081, and the color map 1201 is switched.

Further, it is also possible that the input light source data can be switched depending on the target, and input light source data corresponding to the target are set in the light source information setting unit 0021. Further, it is also possible that the target selection screen is prepared for each of the weight coefficient and the input light source data, and the weight coefficient and the input light source data are independently selected (controlled).

INDUSTRIAL APPLICABILITY

The ultrasound diagnostic apparatus of the present invention has effects that a three-dimensional image that expresses the shading effect due to the leakage, absorption or others of light can be created, and is useful as an ultrasound diagnostic apparatus for generating a three-dimensional projection image from ultrasonic luminance volume data.

REFERENCE SIGNS LIST

0001 ultrasound diagnostic apparatus
0002 ultrasonic probe
0003 control unit
0004 operation unit
0005 sending unit
0006 receiving unit
0007 sending/receiving control unit
0008 beamformer unit
0009 display unit
0011 multi-planar reconstruction (B-mode) region information calculation unit
0012 three-dimensional data storage unit
0013 arbitrary multi-planar reconstruction (B-mode) image creation unit
0014 three-dimensional coordinate transformation unit
0015 volume data storage unit
0016 three-dimensional image processing unit
0017 image composition unit
0018 volume rendering unit
0019 gradient calculation unit
0021 light source information setting unit
0022 optical property setting unit
0023 illuminance calculation unit
0080 illuminance correction unit
0081 corrected optical property setting unit
0082 corrected light source information setting unit
0401 illuminance volume data storage unit
0402 light source data holding unit
0403 two-dimensional convolution processing unit
0404 addition unit
1001 addition unit
1002 corrected illuminance volume data storage unit
1201, 1312, 1313, 1314 color map
1300 graphical interface
1301, 1305 selection screen

The invention claimed is:

1. An ultrasound diagnostic apparatus to display a three-dimensional image of an object based on luminance volume data, the ultrasound diagnostic apparatus comprising:
  a light source information setting unit configured to set light source data indicating a property of a light source that is set in a three-dimensional space;
  an optical property setting unit configured to set a first weight coefficient indicating an optical property of the luminance volume data with respect to the light source;
  an illuminance calculation unit configured to calculate an illuminance at a position corresponding to a coordinate of the luminance volume data, based on the light source data and the first weight coefficient, and to create illuminance volume data based on the calculated illuminance; and a volume rendering unit configured to create the three-dimensional image from the luminance volume data and the illuminance volume data, wherein the optical property setting unit sets the first weight coefficient depending on a luminance of the luminance volume data and a distance from a surface of the object.

2. The ultrasound diagnostic apparatus according to claim 1, wherein the illuminance calculation unit comprises:

a two-dimensional convolution processing unit configured to conduct two-dimensional convolution of the light source data to generate two-dimensional convolution data; and a first weighted addition unit configured to conduct weighted addition of the light source data and the two-dimensional convolution data based on the first weight coefficient to create the illuminance volume data.

3. The ultrasound diagnostic apparatus according to claim 2, wherein the illuminance calculation unit comprises a light source data holding unit configured to hold an initial value of the light source data and a result of the weighted addition by the first weighted addition unit, as input light source data, generates two-dimensional convolution data, by conducting two-dimensional convolution of the input light source data while switching a voxel luminance from an illuminance calculation starting position to an illuminance calculation ending position in the luminance volume data, and creates the illuminance volume data, by conducting weighted addition of the input light source data and the two-dimensional convolution data based on the first weight coefficient.

4. The ultrasound diagnostic apparatus according to claim 1, wherein the volume rendering unit creates the three-dimensional image, based on an opacity to be referred to by an illuminance of the illuminance volume data and a luminance of the luminance volume data.

5. The ultrasound diagnostic apparatus according to claim 1, wherein the first weight coefficient is specified by a two-dimensional weight coefficient table whose indexes are a luminance of the luminance volume data and a distance from a surface of the object.

6. The ultrasound diagnostic apparatus according to claim 1, wherein the light source information setting unit sets the light source data by adjusting at least one of an intensity of the light source, a position of the light source in the three-dimensional space, a direction of the light source, a color tone of the light source, and a shape of the light source.

7. The ultrasound diagnostic apparatus according to claim 1, wherein the light source information setting unit sets the light source data corresponding to a plurality of wavelengths of the light source, the optical property setting unit sets the first weight coefficient for each of the plurality of wavelengths, and the illuminance calculation unit creates the illuminance volume data for each of the plurality of wavelengths.

8. The ultrasound diagnostic apparatus according to claim 1, comprising:

a corrected light source information setting unit configured to set an opposite direction to a visual line direction in the three-dimensional space, as a corrected light source direction, and to set corrected light source data indicating a property of a corrected light source that emits light in the corrected light source direction;

a corrected optical property setting unit configured to set a second weight coefficient indicating an optical property of the luminance volume data with respect to the corrected light source; and an illuminance correction unit configured to calculate an illuminance at a position corresponding to a coordinate of the luminance volume data, based on the corrected light source data and the second weight coefficient, and to create corrected illuminance volume data based on the calculated corrected illuminance, wherein the corrected optical property setting unit sets the second weight coefficient depending on a luminance of the luminance volume data and a distance from a surface of the object, and the volume rendering unit creates the three-dimensional image from the luminance volume data and the corrected illuminance volume data.

9. The ultrasound diagnostic apparatus according to claim 8, wherein the illuminance correction unit comprises:

an addition unit configured to add the corrected light source data and the illuminance volume data;

a two-dimensional convolution processing unit configured to generate two-dimensional convolution data, by conducting two-dimensional convolution of an added value of the corrected light source data and the illuminance volume data; and a second weighted addition unit configured to create the corrected illuminance volume data, by conducting weighted addition of the corrected light source data and the two-dimensional convolution data based on the second weight coefficient.

10. The ultrasound diagnostic apparatus according to claim 1, comprising a display unit configured to display a color map whose indexes are a luminance of the luminance volume data and a distance from a surface of the object, the color map corresponding to a two-dimensional weight coefficient table that specifies the first weight coefficient.

11. The ultrasound diagnostic apparatus according to claim 10, wherein the display unit selectively displays a plurality of the color maps corresponding to a plurality of two-dimensional weight coefficient tables each of which specifies the first weight coefficient corresponding to a tissue of the object.

12. The ultrasound diagnostic apparatus according to claim 2, wherein the two-dimensional convolution processing unit generates a plurality of two-dimensional convolution data, by conducting a plurality of two-dimensional convolution for the light source data.

13. An ultrasound three-dimensional image creation method of displaying a three-dimensional image of an object based on luminance volume data, the ultrasound three-dimensional image creation method comprising:

setting light source data indicating a property of a light source that is set in a three-dimensional space;

setting a weight coefficient indicating an optical property of the luminance volume data with respect to the light source, depending on a luminance of the luminance volume data and a distance from a surface of the object;

calculating an illuminance at a position corresponding to a coordinate of the luminance volume data, based on the optical data and the weight coefficient, and creating illuminance volume data based on the calculated illuminance; and creating the three-dimensional image from the luminance volume data and the illuminance volume data.

* * * * *